United States Patent
Wang et al.

(10) Patent No.: US 10,538,486 B2
(45) Date of Patent: Jan. 21, 2020

(54) HYDROXAMIC ACID TYPE CONTRAST AGENT CONTAINING RADIOISOTOPE FLUORIDE, PREPARATION METHOD AND APPLICATION THEREOF

(71) Applicant: Institute of Nuclear Energy Research, Atomic Energy Council, Executive Yuan, R.O.C., Taoyuan (TW)

(72) Inventors: Mei-Hui Wang, Taoyuan (TW); Chia-Yu Hu, Taoyuan (TW); Mao-Chi Weng, Taoyuan (TW); Jyun-Hong Chen, Taoyuan (TW); Chun-Hung Yang, Taoyuan (TW); Hung-Man Yu, Taoyuan (TW)

(73) Assignee: INSTITUTE OF NUCLEAR ENERGY RESEARCH, ATOMIC ENERGY COUNCIL, EXECUTIVE YUAN. R.O.C, Taoyuan (TW)

( * ) Notice: Subject to any disclaimer, the term of this patent is extended or adjusted under 35 U.S.C. 154(b) by 113 days.

(21) Appl. No.: 15/795,600

(22) Filed: Oct. 27, 2017

(65) Prior Publication Data

US 2019/0106381 A1     Apr. 11, 2019

(30) Foreign Application Priority Data

Oct. 11, 2017   (TW) ............................... 106134788 A

(51) Int. Cl.
| | | |
|---|---|---|
| A61K 51/00 | (2006.01) | |
| A61M 36/14 | (2006.01) | |
| C07C 259/06 | (2006.01) | |
| C07B 59/00 | (2006.01) | |
| A61K 51/04 | (2006.01) | |
| C07C 205/37 | (2006.01) | |

(52) U.S. Cl.
CPC ........ *C07C 259/06* (2013.01); *A61K 51/0402* (2013.01); *C07B 59/001* (2013.01); *C07C 205/37* (2013.01); *C07B 2200/05* (2013.01)

(58) Field of Classification Search
CPC .... C07C 259/06; C07B 2200/05; A61K 51/04
USPC ...................................................... 424/1.89
See application file for complete search history.

(56) References Cited

U.S. PATENT DOCUMENTS

2009/0291978 A1* 11/2009 Davidson .............. C07C 259/06
                                                                514/300

FOREIGN PATENT DOCUMENTS

| CN | 102786448 A | 11/2012 |
| EP | 2349985 A2 | 8/2011 |

OTHER PUBLICATIONS

Hendericks et al. J. Med. Chem. 2011, 54, 5576-5582.*
Park et al. ChemMedChem May 2010, 591-597.*
Wood et al. Mol. Cancer Ther. 2010, 246-256.*
Zhang et al. Bioorg. Med. Chem. 2013, 6981-6995.*
Williamson Macro. Micro. Org. Exper. Jan. 5, 1994.*
Prescription information—ZOLINZA (vorinostat) Capsules, 2006.
Prescription information—BELEODAQ (belinostat) for injection, 2014.
Uday Mukhopadhyay et al., Radiosynthesis of 6-([18F]fluoroacetamido)-1-hexanoic-anilide ([18F]FAHA) for PET Imaging of Histone Deacetylase (HDAC), L label Compd Radiopharm, 2006, 49, 997-1006.
Hendricks, J. A. et al., In vivo PET Imaging of Histone Deacetylases by 18F-Suberoylanilide Hydroxamic Acid (18F-SAHA), Journal of Medicinal Chemistry, 2011, 54, 5576-5582.
Park, H. et al., A Structure-Based Virtual Screening Approach toward the Discovery of Histone Deacetylase Inhibitors: Identification of Promising Zinc-Chelating Groups, ChemMedChem, May 2010, 591-597.
Frey, Robin R et al., Trifluoromethyl Ketones as inhibitors of Histone Deacetylase, Bioorganic & Medicinal Chemistry Letters, Dec. 2002, 3443-3447.
Gediya, L. K. et al., A New Simple and High-Yield Synthesis of Suberoylanilide Hydroxamic Acid and Its Inhibitory Effect Alone or in Combination with Retinoids on Proliferation of Human Prostate Cancer Cells, Journal of Medicinal Chemistry, 2005, vol. 48, No. 15, 5047-5051.

* cited by examiner

*Primary Examiner* — Michael G. Hartley
*Assistant Examiner* — Sean R Donohue
(74) *Attorney, Agent, or Firm* — Locke Lord LLP; Tim Tingkang Xia, Esq.

(57) ABSTRACT

The present invention relates to a hydroxamic acid-based contrast agent containing an isotope of fluorine, which comprises a compound having a structure of Formula (III):

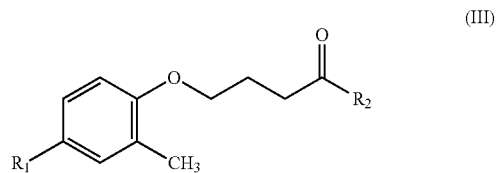

(III)

wherein $R_1$ represents radioactive fluorine-18 ($^{18}F$) or isotope fluorine-19 ($^{19}F$), and $R_2$ represents hydroxyamine —(NH)OH. The hydroxamic acid-based contrast agent containing an isotope of fluorine provided in the present invention has the capability of selectively inhibiting histone deacetylase (HDAC) subtypes 8/6/3, and specifically targets to the focus of spinocerebellar ataxia with over-activation of HDAC. By labeling with the radioisotope fluorine-18, a positron emission tomography (PET) image is obtained with the hydroxamic acid-based contrast agent containing radioisotope fluorine-18, whereby spinocerebellar ataxia is effectively detected. Therefore, the hydroxamic acid-based contrast agent containing an isotope of fluorine provided in the present invention is potentially useful as a probe for early diagnosis and evaluation of the therapeutic effect of spinocerebellar ataxia.

2 Claims, 5 Drawing Sheets

MRI images 6 week old     8 week old

TG

WT

HYDROXAMIC ACID TYPE CONTRAST AGENT CONTAINING RADIOISOTOPE FLUORIDE, PREPARATION METHOD AND APPLICATION THEREOF

CROSS-REFERENCE TO RELATED APPLICATION

This application also claims priority to Taiwan Patent Application No. 106134788 filed in the Taiwan Patent Office on Oct. 11, 2017, the entire content of which is incorporated herein by reference.

TECHNICAL FIELD

The present disclosure relates to a hydroxamic acid-based contrast agent containing an isotope of fluorine, and more particularly to a contrast agent useful in the diagnosis of spinocerebellar ataxia.

BACKGROUND

In August, 2000, Rare Disease Control and Orphan Drug Act was promulgated, in which associated regulations about rare diseases were formulated. By Dec. 31, 2015, the National Health Department, Ministry of Health and Welfare Department of the Executive Yuan announced a total of 205 rare diseases. Spinocerebellar ataxia is one of the rare genetic diseases, and included in the major injury and disease category 07, with a rare disease classification serial number 334.3. The prevalence of spinocerebellar ataxia varies from species to species and from country to country. The incidence in the United States is estimated to be about 3-5 cases in every 100,000 people, and about 10 thousands of people suffer from spinocerebellar ataxia in Taiwan, constituting the largest population among all the people with various rare diseases.

At present, there is no effective diagnosis and treatment for spinocerebellar ataxia, and the symptoms are relieved and the deterioration of the disease is slowed down only through a variety of rehabilitation treatments. Therefore, it is necessary to develop a drug for the diagnosis and treatment of spinocerebellar ataxia, in which a histone deacetylase (HDAC) inhibitor having the effect of modifying transcriptional disorder is of great potential.

HDAC mainly functions to deacylate the lysine on the histone protein, and affects the function of intracellular proteins. When the HDAC activity is out of balance, many diseases, such as cancers and neurodegenerative diseases are caused.

Depending on different structures, the HDAC inhibitors are divided into four types, including hydroxamic acid-based, cyclotetrapeptide-based, phenyl amide-based and short chain fatty acid-based HDAC inhibitors. Among them, the hydroxamic acid-based HDAC inhibitors SAHA (Vorinostat, Zolinza™, Merk) and Belinostat (PXD101, Novartis) are approved by FDA respectively in 2006 and 2014 for treating T cell lymphoma, which can also exhibit good therapeutic effect in the treatment of a variety of cancers while the injury to normal tissues is little. It is further pointed out in literatures that the symptoms can be improved by targeting HDAC in the treatment of neurodegenerative diseases.

The HDAC inhibitor is labeled with a radioactive isotope by a radiochemical method, and the distribution of the agent in vivo is traced by non-invasive imaging to evaluate the therapeutic effect during the treatment of diseases. This facilitates the development of new drugs of such inhibitors. Among a variety of radioactive isotopes, fluorine-18 is most widely used in the research of nuclear medicine and in clinic, and considered as a desirable nuclide for non-invasive imaging, due to the good properties such as suitable half-life (110 minutes) such that there is sufficient time to carry out the above-mentioned relatively complex chemical synthesis steps, and a high-resolution image can be obtained. After being injected to the lateral ventricles of animals, the fluorine-18-hydroxamic acid-based compound can target a focus of spinocerebellar ataxia with over-activation of HDAC, and a positron emission tomography (PET) image is obtained by taking advantage of the radioactivity of fluorine-18, thus providing early diagnosis or evaluation for the therapeutic effect during the treatment of diseases.

The studies on detection of over activated HDAC by using the fluorine-18 labeling technology in related art include "Non-invasive imaging for histone deacetylase with contrast agent fluorine-18-FAHA for cancer cells in animals", Uday et al. J. Label. Compd. Radiopharm; 49: 997-1006, 2006.

However, fluorine-18-FAHA has the disadvantage of rapid metabolization into fluoro-18-fluoroacetate (FAC) in vivo. This metabolite is easily absorbed by the glial cells or peripheral tissue, such that the imaging results are affected, and whether the radioactive isotope fluorine detected by the image is the distribution of fluorine 18-FAHA or fluorine 18-FAC cannot be determined. In addition, fluorine 18-FAHA does not have the functional group acylhydroxylamine, and can only sever as a substrate, rather than an inhibitor, of HDAC.

In 2011, J. Adam Hendricks et al proposed a method for preparing fluorine-18-SAHA (J Med Chem. 11; 54(15): 5576-5582.), in which fluorine-18-SAHA is determined to have a HDAC inhibition function, and confirmed to have a targeting effect in a tumor animal model. However, there are still limitations on fluorine-18-SAHA. Because SAHA is a broad-spectrum inhibitor and has an inhibitory effect on all the subgroups of HDAC, it is difficult to distinguish the role of individual subtypes in the development of diseases. Moreover, the process for labeling with fluorine-18 comprises 3-step synthesis including fluorination of aniline, bonding with dimethyl suberate, and formation of hydroxamic acid, as well as purification. The operation steps are complex, the risk of exposure to radiation is increased, and the radioactive labeling yield is quite low.

In view of this, there is unmet need for developing a new hydroxamic acid-based contrast agent containing an isotope of fluorine, to solve the above problems.

SUMMARY

An object of the present invention provides a hydroxamic acid-based contrast agent containing an isotope of fluorine, which comprises a compound having a structure of Formula (III):

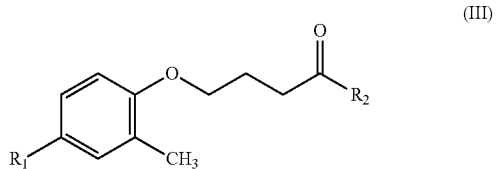

(III)

where $R_1$ represents radioactive fluorine-18 ($^{18}F$) or isotope fluorine-19 ($^{19}F$), and $R_2$ represents hydroxyamine —(NH)OH.

Another object of the present invention is to provide a precursor of the hydroxamic acid-based contrast agent containing an isotope of fluorine according to claim 1, which comprises a compound having a structure of Formula (I):

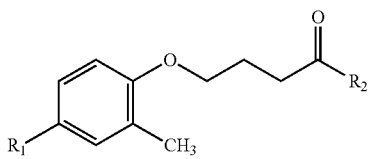

where $R_1$ represents nitro, and $R_2$ represents methoxy.

A further object of the present invention is to provide a method for preparing a hydroxamic acid-based contrast agent containing an isotope of fluorine, which comprises: Step I: preparing a precursor that is the precursor as described above, by dissolving 4-nitro-2-methoxyphenol, methyl 4-bromobutyrate, and potassium carbonate in dimethyl formamide, and reacting at 60-90° C. for 12-36 hrs; then adding ethyl acetate, and extracting with a saturated sodium bicarbonate solution, an aqueous hydrochloric acid solution, and a saturated saline; and collecting the organic layer, removing water, concentrating under reduced pressure, filtering, and purifying by column chromatography on silica gel, to obtain the precursor as a yellow solid; Step II: fluorinating the prepared precursor to produce an intermediate product; and Step III: subjecting the intermediate product to a hydroxamic acid forming reaction, to form the final product.

Compared with the prior art, the present invention has mainly the following beneficial effects. 1. The hydroxamic acid-based contrast agent containing an isotope of fluorine provided in the present invention has the capability of selectively inhibiting histone deacetylase subtypes 8/6/3, and has a stability of at least 6 hrs without decomposition after fluorination of fluorine-18. 2. The hydroxamic acid-based contrast agent containing an isotope of fluorine provided in the present invention is specifically accumulated and targets at a site with over-activated histone deacetylases (HDAC) caused by spinocerebellar ataxia. 3. The preparation process is simple and lowly hazardous, which facilitates this HDAC targeting inhibitor translation further as a new drug for treating and diagnosing spinocerebellar ataxia.

DETAILED DESCRIPTION OF DISCLOSED EMBODIMENTS

Preferred embodiments or examples are provided in the present invention for illustrating the technical means adopted for solving the problems, instead of limiting the scope of the claims of the present invention. Equivalent changes and modifications made in accordance with and without departing from the scope of the present invention are covered in the present invention.

The present invention provides a hydroxamic acid-based contrast agent containing an isotope of fluorine, which comprises a compound having a structure of Formula (III):

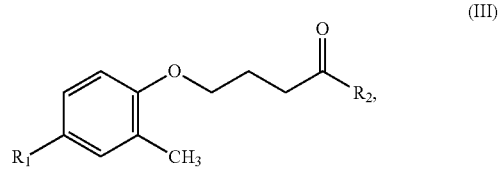

where $R_1$ represents radioactive fluorine-18 ($^{18}F$) or isotope fluorine-19 ($^{19}F$), and $R_2$ represents hydroxyamine —(NH)OH.

When $R_1$ is radioactive fluorine-18 ($^{18}F$), the compound is a fluorine-18-hydroxamic acid-based compound having radioactivity; and when $R_1$ is the isotope fluorine-19 ($^{19}F$), the compound is a fluorine-19-hydroxamic acid-based compound having no radioactivity.

Based on the foregoing, the fluorine-18-hydroxamic acid-based compound or the fluorine-19-hydroxamic acid-based compound comprised in the hydroxamic acid-based contrast agent containing an isotope of fluorine provided in the present invention is obtained by fluorinating a compound having a structure of Formula (I)

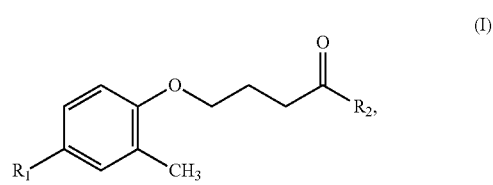

where $R_1$ represents nitro, and $R_2$ represents methoxy. and then subjecting the fluorinated product to a hydroxamic acid forming reaction.

In other words, the compound having a structure of Formula (I) is a precursor of the hydroxamic acid-based contrast agent having an isotope of fluorine.

Methods for preparing the hydroxamic acid-based contrast agent having an isotope of fluorine and the precursor thereof are further described below. Herein, the hydroxamic acid-based contrast agent having an isotope of fluorine is exemplified with a fluorine-18-hydroxamic acid-based compound.

EXAMPLE 1.

Preparation of the Compound with a Structure of Formula (I)

Figure 1:
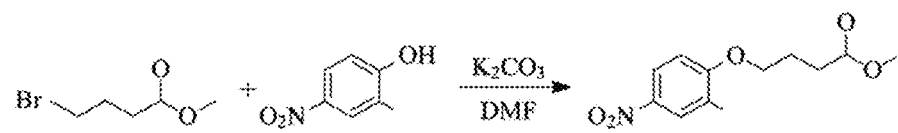
FIG. 1 shows a reaction scheme for synthesizing a precursor of Formula (I) of a fluorine-18-hydroxamic acid-based compound according to the present invention.

FIG. 1 shows a reaction scheme for synthesizing a precursor of Formula (I) of a fluorine-18-hydroxamic acid-based compound according to the present invention. 4-nitro-2-methoxyphenol (1.53 g, 8.2 mmol, 1.0 eq), 4-methyl bromobutyrate (1.98 g, 11.0 mmol, 1.3 eq) and potassium carbonate (2.76 g, 20.0 mmol, 2.4 eq) were dissolved in dimethyl formamide (25 mL) and reacted overnight at 80° C. with stirring. Ethyl acetate (100 mL) was added, and extracted with a saturated sodium bicarbonate solution (100 mL), a 1 N aqueous hydrochloric acid solution (100 mL), and a saturated saline (100 mL). The organic layer was collected, removed of water with magnesium sulfate, concentrated under reduced pressure, filtered, and finally purified by column chromatography on silica gel using ethyl acetate/n-hexane (30:70) as a mobile phase, to obtain a precursor as a yellow solid of a fluorine-18-hydroxamic acid-based compound (2.26 g, yield 96%). $^1$H NMR (300 MHz, D2O, δ): 8.10-8.03 (m, 2H), 6.86-6.83 (d, J=8.7 Hz, 1H), 4.15-4.11 (t, J=6.3 Hz, 2H), 3.70 (s, 3H), 2.59-2.55 (t, J=7.2 Hz, 2H), 2.27 (s, 3H), 2.22-2.17 (m, 2H).

EXAMPLE 2.

Preparation of the Compound with a Structure of Formula (III)

Figure 2:
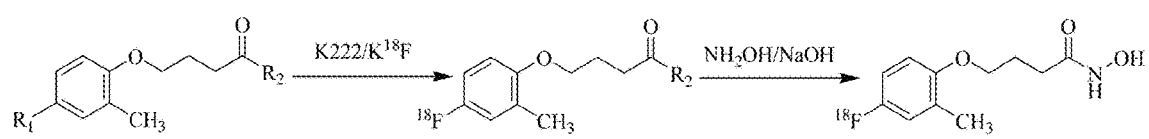
FIG. 2 shows a reaction scheme for fluorinating a precursor of Formula (I) of a fluorine-18-hydroxamic acid-based compound according to the present invention and then producing a hydroxamic acid with the fluorinated product.

The compound with a structure of Formula (III) is obtained by fluorinating the compound having a structure of Formula (I) and then subjecting the fluorinated product to a hydroxamic acid forming reaction. FIG. 2 shows a reaction scheme for fluorinating a precursor of Formula (I) of a fluorine-18-hydroxamic acid-based compound according to the present invention and then producing a hydroxamic acid with the fluorinated product. FIG. 2 shows a reaction scheme for fluorinating the precursor of Formula (I) of a fluorine-18-hydroxamic acid-based compound according to the present invention and then producing a hydroxamic acid with the fluorinated product.

An aqueous solution of fluorine-18 (200 mCi) was passed through QMA ion exchange resin, and then Krytofix2.2.2/potassium carbonate (1 ml, acetonitrile/water:85:15) was further passed through QMA. The Krytofix2.2.2[K$^{18}$F] solution was collected in a reaction flask, sealed, and evaporated to dryness at 110° C. with introduction of nitrogen. Then, anhydrous acetonitrile (2.4 ml) was slowly added to the reaction flask in three portions, and azeotropically evaporated to dryness. The prepared precursor of Formula (I) (the compound with a structure of Formula (I)) of the fluorine-18-hydroxamic acid-based compound was dissolved in anhydrous acetonitrile (1 ml), added to the reaction flask and reacted for 20 min at 110° C., to obtain an intermediate product with a structure of Formula (II) below, which is a crude fluorine-18-product:

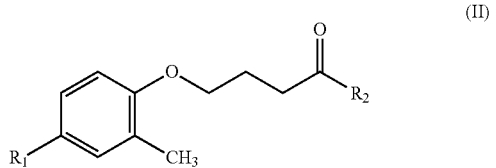

(II)

where $R_1$ represents radioactive fluorine-18 ($^{18}$F) or isotope fluorine-19 ($^{19}$F), and $R_2$ represents methoxy.

Figure 3:
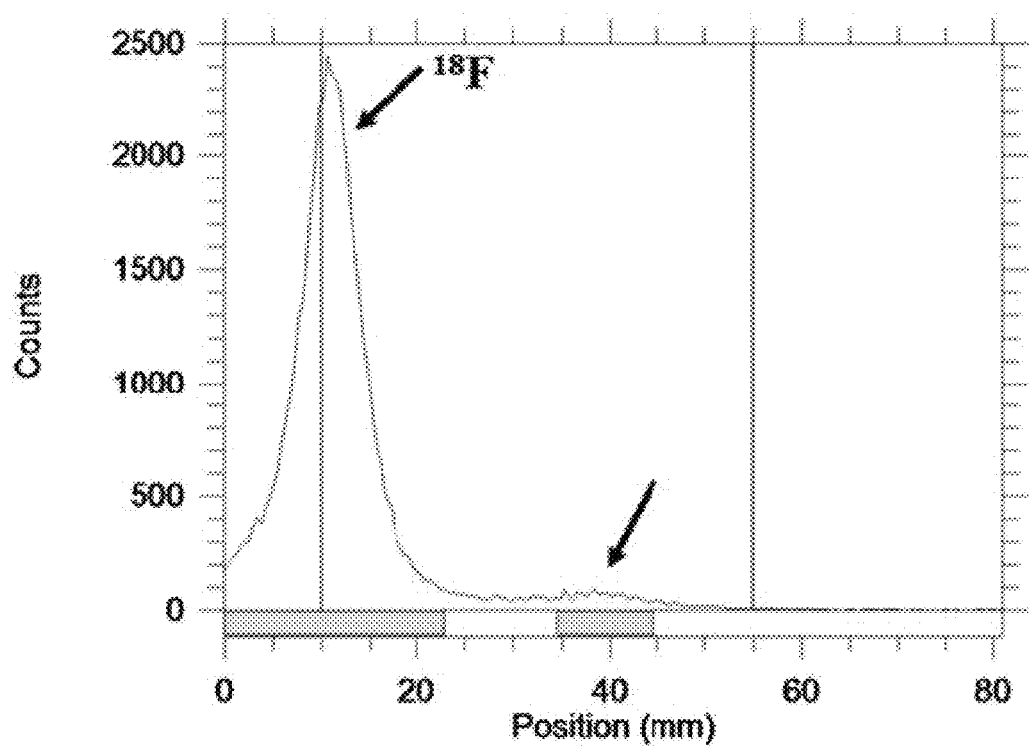
FIG. 3 shows TLC analysis of a fluorine-18-hydroxamic acid-based intermediate product of Formula (II) according to the present invention.

The crude fluorine-18-product was cooled to room temperature and analyzed by thin layer chromatography (TLC) using ethyl acetate/hexane=2/4(v/v) as a developing phase, in which Rf is 0.7 (as shown in FIG. 3).

Then, the crude fluorine-18-product (the compound with a structure of Formula (II)) was evaporated to dryness, and then hydroxyamine (250 μL, 4.0 M in MeOH) and sodium hydroxide (750 μL, 1.0 M in MeOH) were added, and subjected to a hydroxamic acid forming reaction for 10 min at 40° C., to obtain the final product fluorine-18-hydroxamic acid-based compound.

Figure 4:
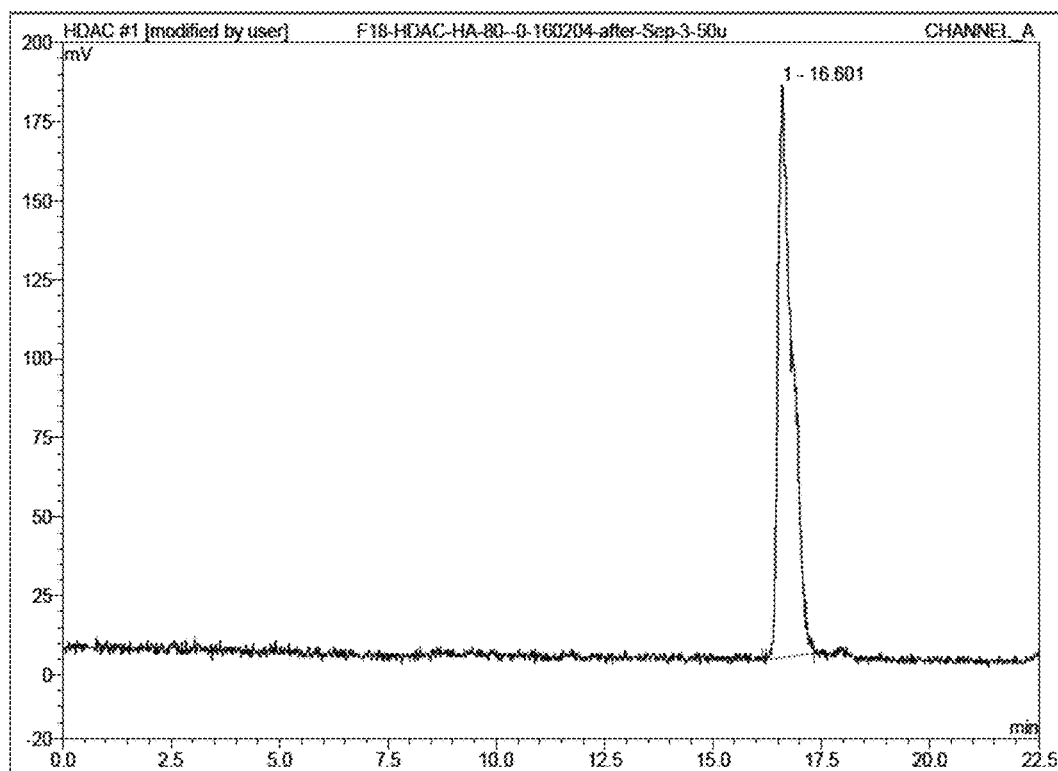
FIG. 4 shows HPLC analysis of a fluorine-18-hydroxamic acid-based compound of Formula (III) according to the present invention.

The fluorine-18-hydroxamic acid-based compound was neutralized with 1.0 M hydrochloric acid, purified by running through a C18 cartridge, and then analyzed by radio-HPLC, where the flow rate is 2 ml/min, and the mobile phase is 80% water (with 0.1% trifluoroacetic acid)/20% acetonitrile. The experimental result shows that the fluorine-18-hydroxamic acid-based compound appears at about 16.6 min (as shown in FIG. 4).

EXAMPLE 3.

Assay of the Inhibitory Effect on Histone Deacetylases (HDAC)

To further investigate whether the fluorine-18-hydroxamic acid-based compound is useful as a HDAC inhibitor, the inhibitory effect on HDAC is assayed with the fluorine-19-hydroxamic acid-based compound. The fluorine-18-hydroxamic acid-based compound and the fluorine-19-hydroxamic acid-based compound have the same chemical properties, except that the fluorine-18-hydroxamic acid-based compound has radioactivity, and the fluorine-19-hydroxamic acid-based compound has no radioactivity.

The fluorine-19-hydroxamic acid-based compound was diluted in dimethyl sulfoxide (DMSO) to give 4 different concentrations. The enzyme activity of various subtypes of HDAC was assayed with a HDAC Fluorometric Assay Kit (available from Enzolifesciences). The fluorine-19-hydroxamic acid-based compound (10 μL) and enzyme (15 μL) were added to a white opaque 96-well plate, and then a substrate (25 μL) was added and incubated for 30 min at room temperature. After incubation, the fluorescence intensity of the 96-well plate was measured on a microplate reader at an excitation wavelength of 355 nm and an emission wavelength of 460 nm, and the fluorescence intensity measured was analyzed by Graph Pad Prism 6 to calculate IC50 (as shown in FIG. 5).

Figure 5:
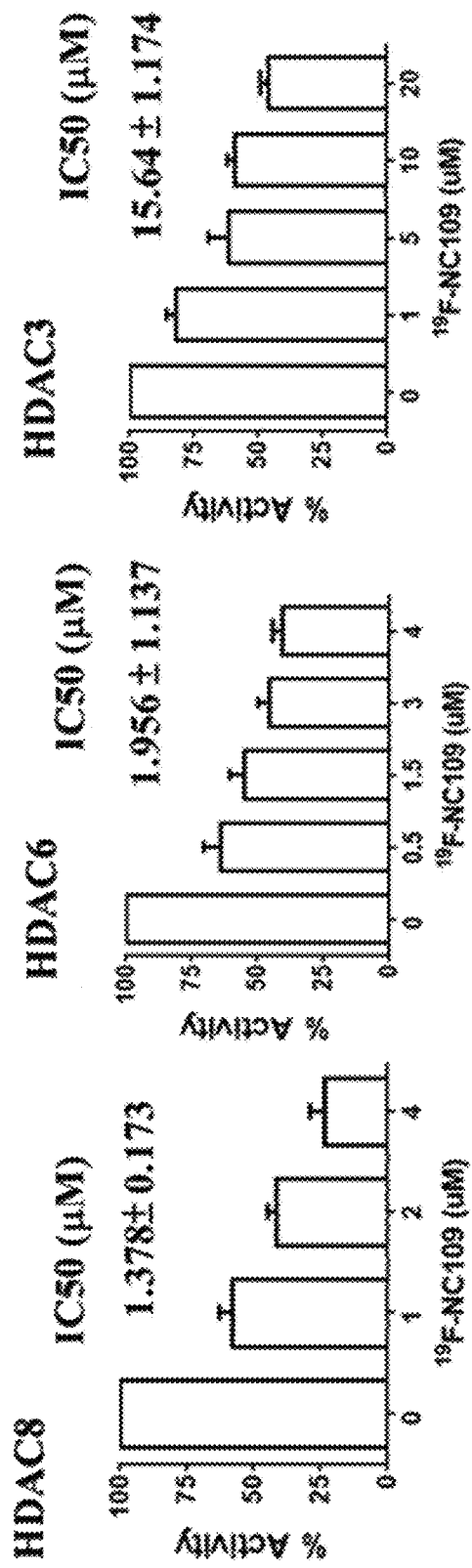
FIG. 5 shows test results of the inhibitory effect of a fluorine-19-hydroxamic acid-based compound of Formula (III) according to the present invention on histone deacetylases (HDAC)

It can be seen from FIG. 5 that the fluorine-19-hydroxamic acid-based compound has an IC50 at which the HDAC8, HDAC6, and HDAC3 are selectively inhibited.

EXAMPLE 4.

Non-Invasive Imaging of Animal Model of Spinocerebellar Ataxia

Figure 6:
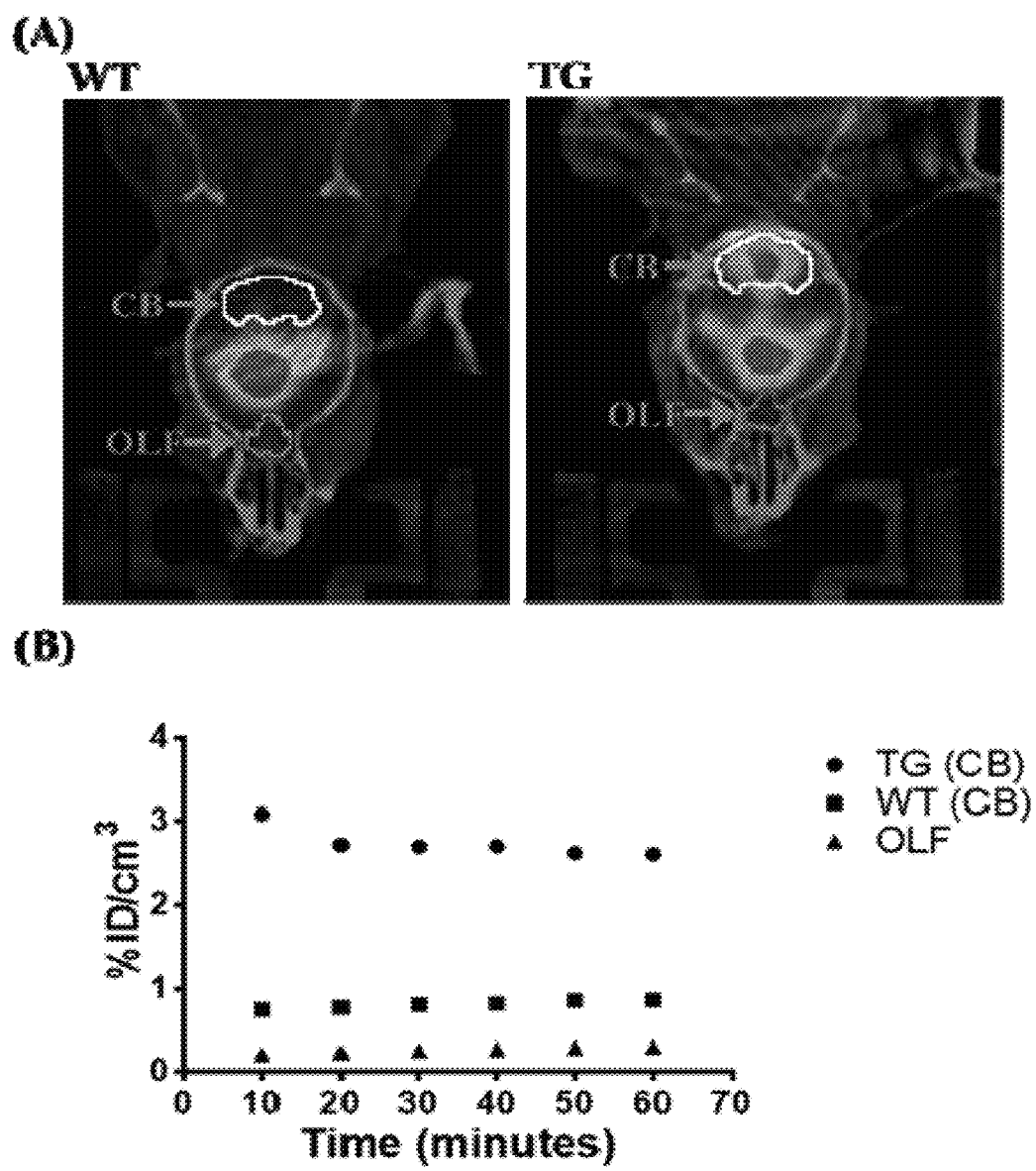
FIG. 6 shows distribution by positron emission tomography (PET) imaging after a fluorine-18-hydroxamic acid-based compound of Formula (III) according to the present invention is injected to lateral ventricles of normal and sick mice (spinocerebellar ataxia)
Figure 7:
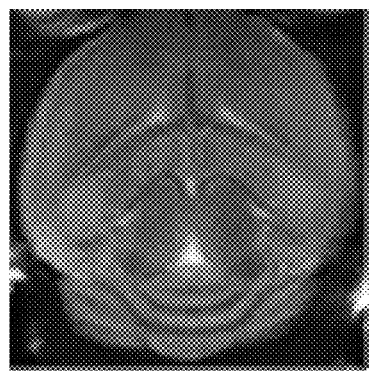
FIG. 7 shows MRI images of 6-week and 8-week old normal and sick mice used in the present invention.
Figure 7:
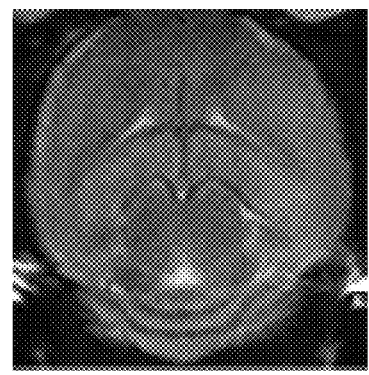
Figure 7:
Figure 7:
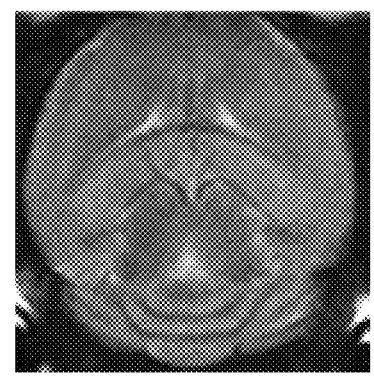

The model mice (SCA17) of spinocerebellar ataxia were anaesthetized with a gas, and then the fluorine-18-hydroxamic acid-based compound (molecular imaging agent) (2 μL, 0.75 MBq, 20 μCi) was injected by means of a stereotaxic apparatus to lateral ventricles of the mice. The distribution of the molecular imaging agent in the mice was scanned by high-resolution positron emission tomography/computed tomography (PET/CT) imaging for 1 hr, to observe the distribution of the agent in brain. The CT and PET images were overlapped and fused, and the ROI was circled by the Pmod software. The result shows that the agent is accumulated in a site in cerebellum of the mice with spinocerebellar ataxia, indicating that the agent has good targeting (as shown in FIG. 6). However, the MRI result shows that there is no significant difference between the cerebellum sizes of normal and sick mice, as shown in FIG. 7, in which TG represents sick mice and WT represents normal mice.

Based on the above experimental results, the hydroxamic acid-based contrast agent containing an isotope of fluorine-18 provided in the present invention is useful as a diagnostic contrast agent for targeting and imaging spinocerebellar ataxia.

What is claimed is:

1. A method for preparing a hydroxamic acid-based contrast agent containing an isotope of fluorine, comprising:

Step I: preparing a precursor by dissolving 2-methyl-4-nitrophenol, methyl 4-bromobutyrate, and potassium carbonate in dimethyl formamide, wherein the molar ratio of the 2-methyl-4-nitrophenol, the 4-methyl bromobutyrate and the potassium carbonate is 8.2:11:20, and reacting at 60-90° C. for 12-36 hrs, wherein the precursor has a structure of Formula (I):

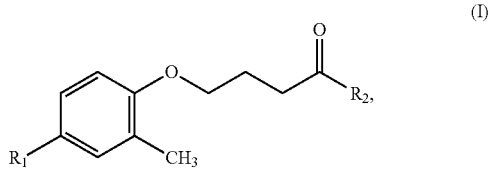

(I)

wherein $R_1$ is nitro, and $R_2$ is methoxy; then adding ethyl acetate, and extracting with a saturated sodium bicarbonate solution, an aqueous hydrochloric acid solution, and a saturated saline; and collecting the organic layer, removing water, concentrating under reduced pressure, filtering, and purifying by column chromatography on silica gel, to obtain the precursor as a yellow solid;

Step II: fluorinating the prepared precursor to produce an intermediate product wherein the intermediate product is a compound having a structure of Formula (II):

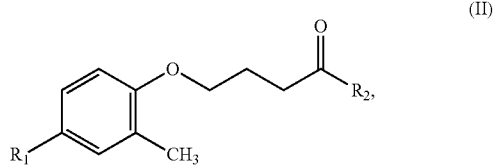

(II)

wherein $R_1$ is radioactive fluorine-18 ($^{18}F$) or isotope fluorine-19 ($^{19}F$), and $R_2$ is methoxy; and Step III: subjecting the intermediate product to a hydroxamic acid forming reaction, to form the final product which has a structure of Formula (III):

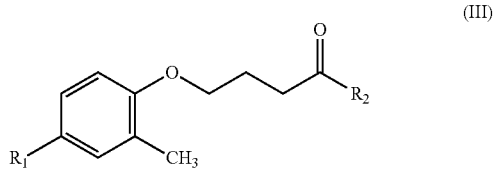

(III)

wherein $R_1$ is radioactive fluorine-18 ($^{18}F$) or isotope fluorine-19 ($^{19}F$), and $R_2$ is —(NH)OH, and wherein the hydroxamic acid forming reaction comprises reacting the intermediate product, hydroxylamine, and sodium hydroxide for 5-20 min at 30-50° C.

2. The method for preparing a hydroxamic acid-based contrast agent containing an isotope of fluorine according to claim 1, wherein the fluorination comprises reacting Fluorine-18 with the precursor for 10-30 min at 100-120° C.

* * * * *